United States Patent
Van de Wouw et al.

(10) Patent No.: US 10,143,521 B2
(45) Date of Patent: *Dec. 4, 2018

(54) SKIN TREATMENT APPARATUS

(71) Applicant: KONINKLIJKE PHILIPS N.V., Eindhoven (NL)

(72) Inventors: Doortje Van de Wouw, Eindhoven (NL); Aleksey Anatolievich Kharin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 289 days.

This patent is subject to a terminal disclaimer.

(21) Appl. No.: 14/768,282

(22) PCT Filed: Mar. 14, 2014

(86) PCT No.: PCT/IB2014/059775
§ 371 (c)(1),
(2) Date: Aug. 17, 2015

(87) PCT Pub. No.: WO2014/147532
PCT Pub. Date: Sep. 25, 2014

(65) Prior Publication Data
US 2016/0058509 A1 Mar. 3, 2016

Related U.S. Application Data

(60) Provisional application No. 61/804,292, filed on Mar. 22, 2013.

(51) Int. Cl.
*A61B 18/20* (2006.01)
*A61B 17/00* (2006.01)
*A61B 18/00* (2006.01)

(52) U.S. Cl.
CPC .. *A61B 18/203* (2013.01); *A61B 2017/00075* (2013.01); *A61B 2018/00452* (2013.01);
(Continued)

(58) Field of Classification Search
CPC ........ A61B 18/203; A61B 2017/00075; A61B 2018/00452; A61B 2018/00642; A61B 2018/2025
(Continued)

(56) References Cited

U.S. PATENT DOCUMENTS 7,105,058 B1 * 9/2006 Sinyagin .................. B05B 5/03
118/61
2006/0158385 A1 * 7/2006 Etelapera .............. G06F 3/1438
345/31
(Continued)

FOREIGN PATENT DOCUMENTS

CN 102499755 A 6/2012
WO 2013011505 A1 1/2013

*Primary Examiner* — Gary Jackson
*Assistant Examiner* — Youwon Kahng (57) ABSTRACT

A skin treatment device (100) comprises: —a housing (101); —a treatment action performer (110) arranged within the housing (101) for performing a treatment action on the user's skin (2) through an output window (103); —a speed sensor (120) for sensing a relative speed between the housing and the user's skin; —a control device (140) provided with an associated memory (141) containing information defining a desired displacement speed, the control device receiving an output signal from the speed sensor; —an optical speed deviation indicator system (400; 600) comprising a position reference (411; 101) and means for generating an optical spot (412; 612) of variable position with respect to the position reference. The control device controls the optical speed deviation indicator system on the basis of the output signal received from the speed sensor and the information in its memory.

20 Claims, 7 Drawing Sheets (52) U.S. Cl.
CPC .............. *A61B 2018/00642* (2013.01); *A61B 2018/2025* (2013.01)

(58) Field of Classification Search
USPC ............................................. 600/9; 606/9, 2
See application file for complete search history.

(56) References Cited

U.S. PATENT DOCUMENTS

| | | |
|---|---|---|
| 2007/0129711 A1 | 6/2007 | Altshuler |
| 2007/0198004 A1 | 8/2007 | Altshuler |
| 2008/0196258 A1 | 8/2008 | Kraus |
| 2008/0292151 A1* | 11/2008 | Kurtz .................... A61B 3/10 382/128 |
| 2011/0230817 A1* | 9/2011 | Moy .................... A61B 18/203 604/20 |
| 2012/0283803 A1* | 11/2012 | Liu ..................... A61B 18/203 607/89 |
| 2016/0106505 A1* | 4/2016 | Speelpenning ...... A61N 5/0616 606/131 |

* cited by examiner

SKIN TREATMENT APPARATUS

This application is the U.S. National Phase application under 35 U.S.C. § 371 of International Application No. PCT/IB2014/059775, filed on Mar. 14, 2014, which claims the benefit of U.S. Provisional Application No. 61/804,292 filed on Mar. 22, 2013. These applications are hereby incorporated by reference herein.

FIELD OF THE INVENTION

The present invention relates in general to apparatus for treating skin, of the type comprising a treatment device that is to be manually displaced over the skin. In this context, the term "treatment" is used in the broadest sense. The treatment may involve for instance skin care and/or skin rejuvenation, and may involve for instance removal of hair such as epilation or depilation. The treatment may be for purely cosmetic reasons. In particular, but not exclusively, the present invention relates to optical epilation devices, and the present invention will be explained in more detail for this type of devices.

BACKGROUND OF THE INVENTION

In skin treatment, generally speaking, a skin treatment device contains an active component that acts on the skin. This component, in operation, performs an action on the skin that constitutes the actual treatment. The action may be mechanical, such as for instance in the case of shaving devices, depilation devices, abrasion devices etc. The action may be thermal, such as for instance in the case of optical epilation devices where a laser beam is applied to the skin in order to destroy part of the hair follicles. In the case of optical epilation devices, the prior art comprises flash-type embodiments that generate one light flash or a limited number of flashes, and the user is supposed to hold the device steady during flashing and to displace the device in between flashing. In contrast thereto, the present invention relates to continuously operating devices that need to be displaced continuously. It is noted in this respect that "continuously operating" includes the situation where a device is continuously generating light flashes, so that the device is to be displaced while flashing. In most, if not all, cases where the device is to be displaced over the skin whilst being in operation, optimum results require an optimum displacement speed. It will easily be understood that too high a speed will result in inadequate treatment results, while the user can do damage to his skin if the device is displaced too slowly or, worse, is held still.

It is true that the user manual may inform the user of the optimum speed or optimum speed range, in centimeters per second, but a problem for the user is how to determine that he is actually displacing the device at the right speed. In practice, this means that users have to go through a lengthy learning process before they have developed a "feeling" of correct speed and before they are able to apply the correct speed consistently.

To reduce this problem, solutions have already been proposed where the device is provided with a speed sensor for detecting the relative speed between the device and the skin, and where the device is provided with an indicator giving the user feedback information. However, the prior art solutions have been found to be unsatisfying.

The indicator may give a sound signal. However, it was found that for the average user it is quite difficult to interpret sound signals.

The indicator may give a tactile signal, such as vibrations. However, apart from the disadvantage that the vibrations are inconvenient to the user, it was found that for the average user it is quite difficult to interpret tactile signals.

US-2007/0129771 discloses a device where the indicator gives an optical signal. Different colours are used to indicate "too high", "too low", or "within range". This has disadvantages in that the system is not intuitive, it requires the user to learn which colour has which meaning, and the information given to the user is very coarse.

SUMMARY OF THE INVENTION

A general object of the present invention is to provide an improvement over the prior art, and more particularly to provide a skin treatment device that provides its user with more detailed speed information in a more comfortable and intuitive manner.

According to the present invention, this general object is achieved by means of a skin treatment device comprising: a housing the shape and size of which are such that it can suitably be held by a human hand, the housing having a skin-side to be directed to a user's skin and an output window arranged on the skin-side; a treatment action performer arranged within the housing for performing a treatment action on the user's skin through the output window; a speed sensor for sensing a relative speed between the housing and the user's skin in a device displacement direction parallel to the skin; an optical speed deviation indicator system comprising a position reference and means for generating at least one optical spot of variable position with respect to the position reference; a control device provided with an associated memory containing information defining a desired displacement speed or a desired displacement speed range, the control device being coupled to receive an output signal from the speed sensor and being coupled to provide a control signal to the optical speed deviation indicator system; wherein the control device is adapted to control the optical speed deviation indicator system such as to vary the position of the optical spot on the basis of the output signal received from the speed sensor and the information in the memory.

In an embodiment of the skin treatment device according to the invention, the optical spot is displaceable with respect to the position reference in a direction parallel to said device displacement direction, wherein the control device is adapted to control the optical speed deviation indicator system such that the optical spot is located in front of the position reference, relative to the displacement direction, if the output signal from the speed sensor indicates that a momentary device displacement speed is below the desired displacement speed or displacement speed range, while the optical spot is located behind the position reference, relative to the displacement direction, if the output signal from the speed sensor indicates that the momentary device displacement speed is above the desired displacement speed or displacement speed range. In this embodiment, the optical speed deviation indicator indicates in a very intuitive manner whether the user moves the device too fast or too slow.

In a preferred embodiment of the skin treatment device according to the invention, the control device is adapted to control the optical speed deviation indicator system such that a distance between the optical spot and the position reference, measured in the direction parallel to said device displacement direction, is proportional to a speed difference between the momentary device displacement speed and the desired displacement speed. In this manner, the distance between the momentary optical spot position and the reference position is indicative of, and may be proportional to, a deviation between the momentary speed of the device and the desired speed of the device. Such a type of speed feedback is very intuitive, and users learn to understand this very quickly. The user's understanding may be further enhanced if the control device is adapted to change the colour of the optical spot in conjunction with the position of the optical spot.

In a practical embodiment of the skin treatment device according to the invention, the speed deviation indicator system comprises a display located on the housing, preferably on a side surface of the housing, and a reference mark arranged on the housing, preferably on said side surface. Such a display may comprise a row of LEDs which can be switched on or off individually, while the control device decides which LED to switch on, based on the output signal from the sensor. Such an embodiment is very easy to implement. In a preferred embodiment, the optical spot is projected on the skin at a position adjacent a treatment area of the device. Such an embodiment is most intuitive, because on the one hand the user tends to look at the skin he is treating anyway, and on the other hand the optical spot is now separate from the device itself and informs the user as to how he should adapt the speed to stay with the optical spot.

In order to allow the user to observe the optical speed indication from either side of the device, it is preferred that the optical speed indication is presented in at least two locations on both sides of the device, in the form of two displays mounted in opposite side faces of the device housing or in the form of two light beams projecting two optical spots on the user's skin on opposite sides of the housing.

Further advantageous elaborations of the skin treatment device according to the invention are mentioned in the dependent claims and are discussed in the description of the invention detailed below.

BRIEF DESCRIPTION OF THE DRAWINGS

These and other aspects, features and advantages of the present invention will be further explained by means of the following description of one or more preferred embodiments with reference to the drawings, in which same reference numerals indicate same or similar parts, and in which.

DETAILED DESCRIPTION OF THE INVENTION

Figure 1A:
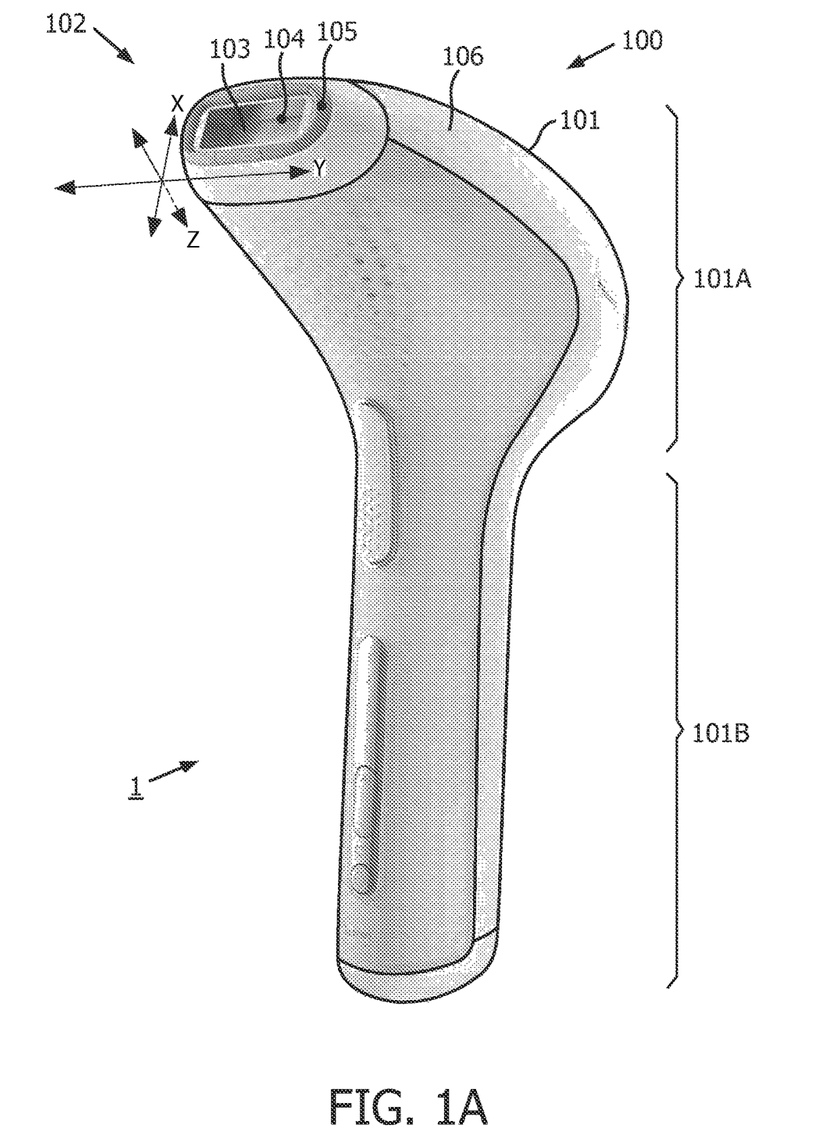
FIG. 1A schematically shows a perspective view of a handheld skin treatment device according to the invention.
Figures 1B, 1C:
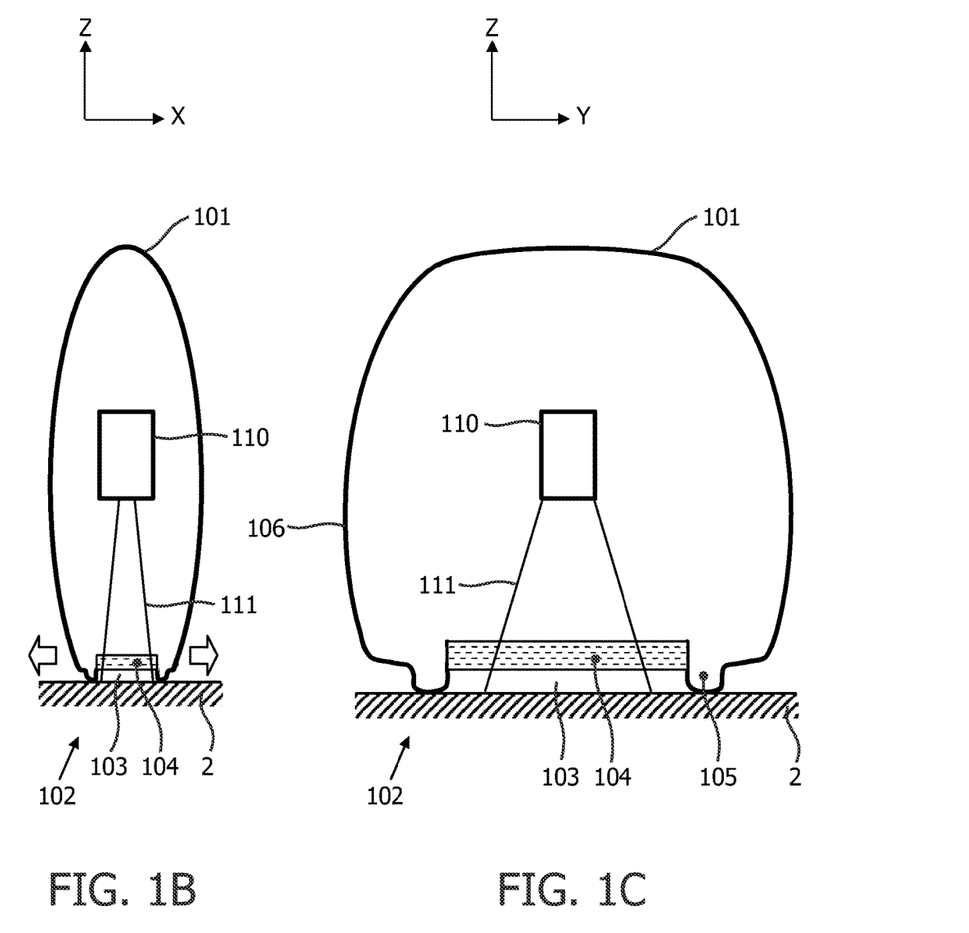
FIGS. 1B and 1C are schematic vertical cross sectional views of the handheld skin treatment device of FIG. 1A in mutually perpendicular directions.

FIG. 1A shows a perspective view of a handheld skin treatment device 100, which is part of a skin treatment apparatus generally indicated by means of reference numeral 1. The skin treatment device 100 has a housing 101. The shape of the housing may be subject to design variations, but in this case the housing has a treatment portion 101A and a grip portion 101B of a size suitable for being held by human hands. In a plan view, the housing 101 may have an elongate profile, which is practical but not essential. FIGS. 1B and 1C are schematic cross sectional views of the treatment portion 101A of the handheld device 100 in mutually perpendicular directions.

In use, the skin treatment device 100 is to be placed on the skin 2 of a user. The side of the housing 101 to be directed to the skin will be indicated as skin-side 102. In FIGS. 1B-1C, this is the underside. Usually, the skin-side 102 of the housing is to be placed on the skin, i.e. actually contacts the skin, although it is possible that contactless devices are used.

In use, the skin treatment device 100 is to be displaced over the skin of a user. It is possible that the skin treatment device 100 may be displaced in any direction parallel to the skin, but in the context of the present invention it will be assumed that the skin treatment device 100 has an intended displacement direction. This intended displacement direction will be indicated as X-direction. In the case of the housing 101 having an elongate profile, the X-direction will typically coincide with the smallest dimension of the housing 101, i.e. the width. The direction parallel to the skin and perpendicular to the X-direction will be indicated as Y-direction, typically coinciding with the longitudinal dimension of the housing 101, i.e. the length. The direction perpendicular to the skin will be indicated as Z-direction, typically coinciding with the height of the housing 101.

FIG. 1B is a cross sectional view according to an XZ-plane, and FIG. 1C is a cross sectional view according to a YZ-plane. The figures illustrate that the housing 101 accommodates an active component indicated as treatment action performer 110. The nature of the treatment action performer 110 depends on the nature of the skin treatment apparatus. In the case of an abrasion device, the treatment may be mechanical, requiring mechanical contact between the treatment action performer 110 and the skin. In the illustrated example, the treatment is optical and the treatment action performer 110 comprises a device for illuminating the skin 2, for instance by scanning an optical beam 111 over the skin or by producing light flashes. The treatment action performer 110 may itself comprise a light source, but it is also possible that the skin treatment apparatus 1 further includes an external light source (not shown for the sake of simplicity), as well as an optical guidance system (for instance based on optical fibres) for transferring the light to the skin treatment device 100. In an example, the treatment caused by the optical beam 111 is epilation by destroying portions of hair follicles, and the present invention specifically relates to an epilation device.

In any case, the skin-side 102 of the housing 101 has an opening 103 through which the treatment action performer 110 can act on the user's skin 2. In the case of an optical action, the opening 103 may be provided with a transparent cover 104 that is substantially transparent to the treatment light 111 but protects the interior of the housing 101 against moisture and dirt. The opening 103 will hereinafter also be indicated as "output window". It is noted that it is not essential that the cover 104 contacts the skin. In cases where the cover 104 tends to become hot, the cover 104 may lie recessed within a surrounding foot portion 105 of the housing 101.

The handheld device as described so far is known in practice. It should be clear that it is important that the skin treatment device 100 is displaced over the skin at a correct speed. This is especially clear in the case of an optical epilation device. The treatment action performer 110 generates light containing a certain amount of energy per unit time, which is distributed over a surface area of the skin 2 corresponding to the size of the output window 103. Taking into account the displacement speed, this corresponds to a certain energy input per square centimeter of skin. If the skin treatment device 100 is displaced too fast, the treatment is inadequate. If the skin treatment device 100 is displaced too slowly, the skin receives too much energy and may be damaged. Thus, the displacement speed should be a correct speed, or should be within a predetermined range of correct speeds. As indicated before, it is very difficult for a user to keep the speed within the limits of such a range.

Figure 2:
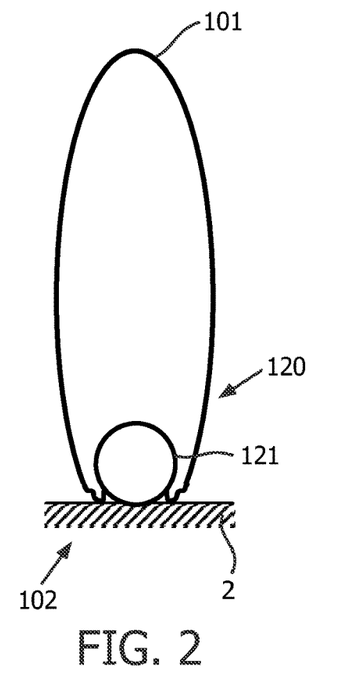
FIG. 2 is a schematic vertical cross sectional view of a handheld skin treatment device.

According to a first aspect of the present invention, the skin treatment device 100 is provided with a speed sensor 120 for sensing the relative speed between the housing 101 and the skin 2. FIG. 2 is a schematic cross sectional view comparable to FIG. 1B, showing the speed sensor 120. For the sake of convenience, the treatment action performer 110 is not shown in this figure. The speed sensor 120 may be any type of sensor, adapted to generate an output signal indicative of or even proportional to the said relative displacement speed. In a possible embodiment, the speed sensor 120 comprises a wheel 121, which touches the skin and is rotated when the housing 101 is displaced. Contact-free speed sensors are also possible, however. In a possible embodiment, the speed sensor 120 comprises an LED for generating a detection beam towards the skin, and an optical detector for detecting reflected light. Speed sensors of this type are known per se, and are for instance used in computer mouses. The speed sensor 120 may be of a kind directly measuring the speed of the housing 101 relative to the skin 2, but may alternatively or in addition comprise a sensor for measuring a displacement of the housing 101 relative to the skin 2, wherein the speed is determined as a mathematical first derivative of the measured displacement, or may alternatively or in addition comprise a sensor for measuring an acceleration of the housing 101 relative to the skin 2, wherein the speed is determined as a mathematical integral of the measured acceleration. Such known sensors can be used in the skin treatment device 100 of the present invention, therefore a more elaborate explanation of the design and operation of the speed sensor is not necessary. It is noted that the LED sensors as used in computer mice are also capable of detecting the relative direction of the displacement, i.e. an angle in the range between 0° and 360° in a virtual plane parallel to the skin.

Figure 3:
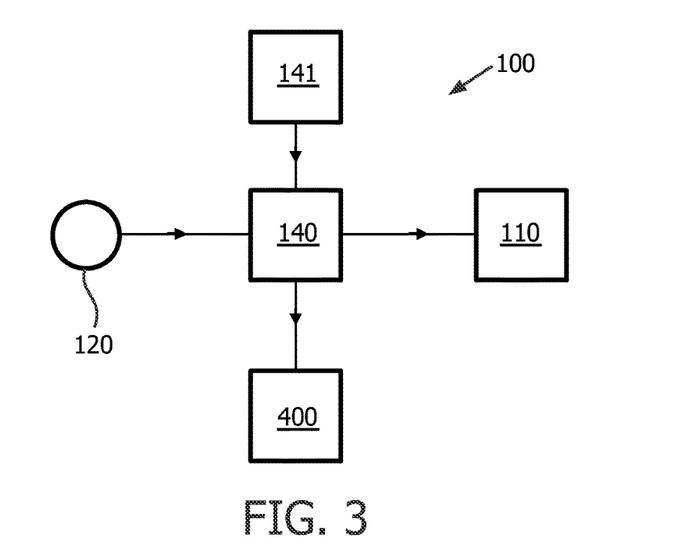
FIG. 3 is a schematic block diagram of a skin treatment device according to the invention.

FIG. 3 is a schematic block diagram showing that the skin treatment device 100 also comprises a control device 140, for instance a suitably programmed microprocessor or controller or the like. The control device 140 has an associated memory 141 containing information defining an optimum speed or an optimum speed range. The control device 140 is coupled to receive an output signal from the speed sensor 120, and is arranged for controlling the treatment action performer 110. Within limits, the control device 140 can reduce the output power of the treatment action performer 110 if the speed is too low, or can increase the output power of the treatment action performer 110 if the speed is too high. However, in general, efficient treatment (e.g. hair removal) requires that the treatment action performer 110 is operated at its nominal output power, so the regulating margin to higher output powers is small. Further, reducing the output power of the treatment action performer 110 at least results in increased treatment time. Best results are achieved if the output power of the treatment action performer 110 is kept close to nominal and the displacement speed is kept close to optimum; and the present invention advantageously provides an intuitive optical speed feedback system 400 displaying to the user an optical indication of a deviation between the momentary displacement speed and the desired speed. The optical indication includes information regarding the magnitude of the deviation (speed difference), and regarding the direction of the deviation, i.e. the sign of the deviation (too slow or too fast). Key of the optical speed feedback system 400 is that it generates an optical spot of variable location, under control of the control device 140. Several embodiments will be discussed below.

Figure 4A:
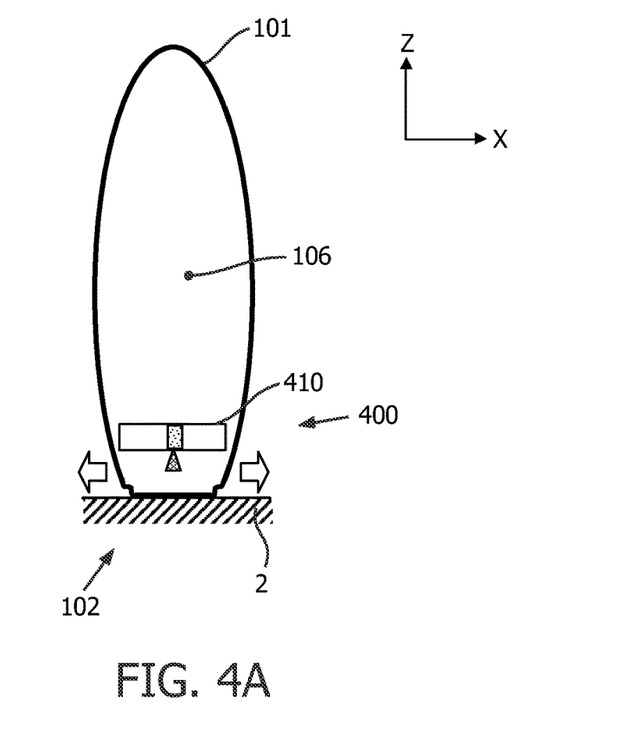
FIG. 4A is a schematic side view of an embodiment of a handheld skin treatment device according to the invention.
Figure 4B:
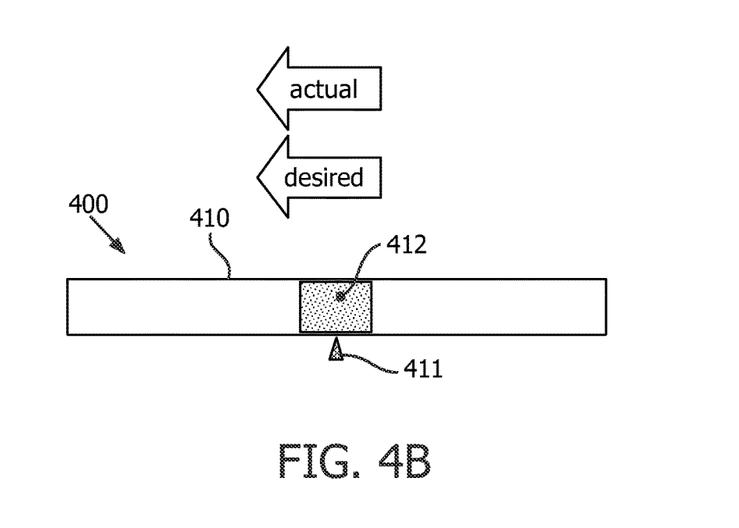
FIG. 4B is a close-up of a display of a skin treatment device according to the invention.

FIG. 4A is a schematic side view taken in the Y-direction of the housing 101, showing that the optical speed feedback system 400, also indicated as speed deviation indicator system 400, comprises a display 410, located on a side surface 106 of the housing 101 at a relatively low position close to the skin-side 102, and FIG. 4B is a close-up of the display 410. The display 410 has an elongate shape, and is arranged in the X-direction. The system 400 further comprises a reference mark 411 arranged on the side surface 106. The figure also shows an optical spot 412 generated on the display 410. The control device 140 is adapted to generate a control signal for the display 410, such that the optical spot 412 is generated at a varying position relative to the reference mark 411.

FIG. 4B shows the display 410 in a situation when the sensor 120 output signal indicates that the skin treatment device 100 is being displaced at a correct speed. By way of illustration, the figure further shows two arrows, one labelled "desired" to indicate the desired speed, and the other labelled "actual" to indicate the actual speed; the arrows have the same length to indicate that the actual speed is correct. The control device 140 generates the control signal for the display 410 such that the position of the optical spot 412 corresponds to the position of the reference mark 411. When the user observes that the position of the optical spot 412 corresponds to the position of the reference mark 411, he knows that he is displacing the skin treatment device 100 at a correct speed. For increased clarity, this optical spot 412a may have a specific colour, for instance green.

Figure 4C:
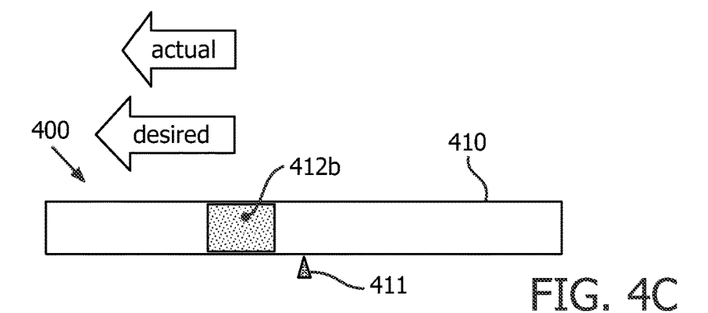
FIGS. 4C-4F show the display of FIG. 4B in several situations.
Figure 4D:
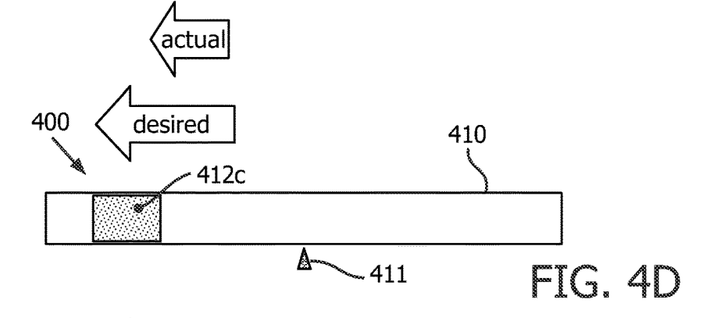

FIG. 4C shows the display 410 in a situation when the sensor 120 output signal indicates that the skin treatment device 100 is being displaced at too low a speed. It is assumed that the displacement is towards the left in the figure. The control device 140 generates the control signal for the display 410 such that the position of the optical spot 412b is displaced with respect to the position of the reference mark 411, wherein the direction of displacement of the optical spot 412b is the same as the direction of displacement of the skin treatment device 100. The larger the speed deviation, the larger the distance between optical spot and reference mark: FIG. 4D shows the optical spot 412c more towards the left, indicating a larger speed deviation. For increased clarity, this optical spot 412b, 412c may change colour with varying position, for instance from yellow to orange to red with increasing distance from the reference mark 411. When the user observes that the position of the optical spot 412 is ahead of the position of the reference mark 411, he knows that he should speed up in order to bring the reference mark 411 closer to the optical spot 412.

Figure 4E:
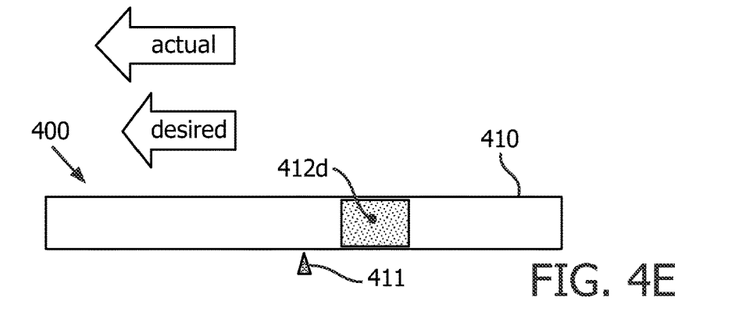
Figure 4F:
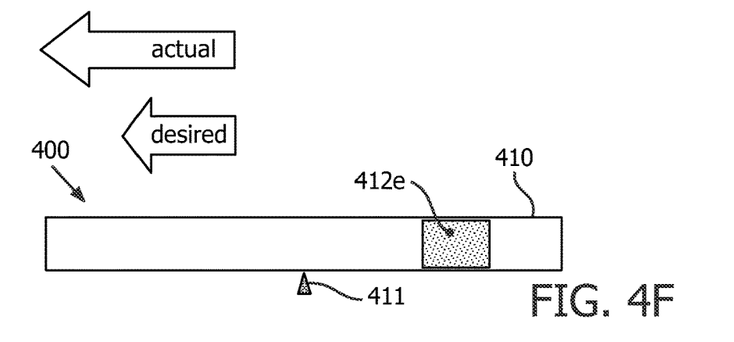

FIG. 4E shows the display 410 in a situation when the sensor 120 output signal indicates that the skin treatment device 100 is being displaced at too high a speed. It is assumed that the displacement is towards the left in the figure. The control device 140 generates the control signal for the display 410 such that the position of the optical spot 412*d* is displaced with respect to the position of the reference mark 411, wherein the direction of displacement of the optical spot 412*d* is opposite to the direction of displacement of the skin treatment device 100. The larger the speed deviation, the larger the distance between optical spot and reference mark: FIG. 4F shows the optical spot 412*e* more towards the right, indicating a larger speed deviation. For increased clarity, this optical spot 412*d*, 412*e* may change colour with varying position, for instance from yellow to orange to red with increasing distance from the reference mark 411. When the user observes that the position of the optical spot 412 is lagging behind the position of the reference mark 411, he knows that he should speed down in order to bring the reference mark 411 closer to the optical spot 412.

The advantageous intuitive nature of the optical speed feedback system 400 of the present invention can be explained as follows. When using the apparatus, the user holds the device 100 in one hand and will look concentrated at the position where the foot 105 of the housing 101 touches his skin. In his field of sight, the display 410 is automatically visible. If the optical spot 412 is moving forward (because the user is displacing the device too slowly), the user just needs to try to move the reference mark towards the optical spot, in other words he is going to increase the displacement speed to catch up with the optical spot. Conversely, if the optical spot 412 is moving backwards (because the user is displacing the device too fast), the user again just needs to try to move the reference mark towards the optical spot, in other words he is going to decrease the displacement speed in order to allow the optical spot to catch up.

Although the present invention is already embodied by a skin treatment device 100 having such a display 410 in one side face, in a preferred embodiment the skin treatment device 100 has two displays in opposite side faces.

In a possible embodiment, the display 410 may comprise a row of LEDs which can be switched on or off individually, while the control device 140 decides which LED in the row to switch on, based on the speed information from the sensor 120.

Figure 5:
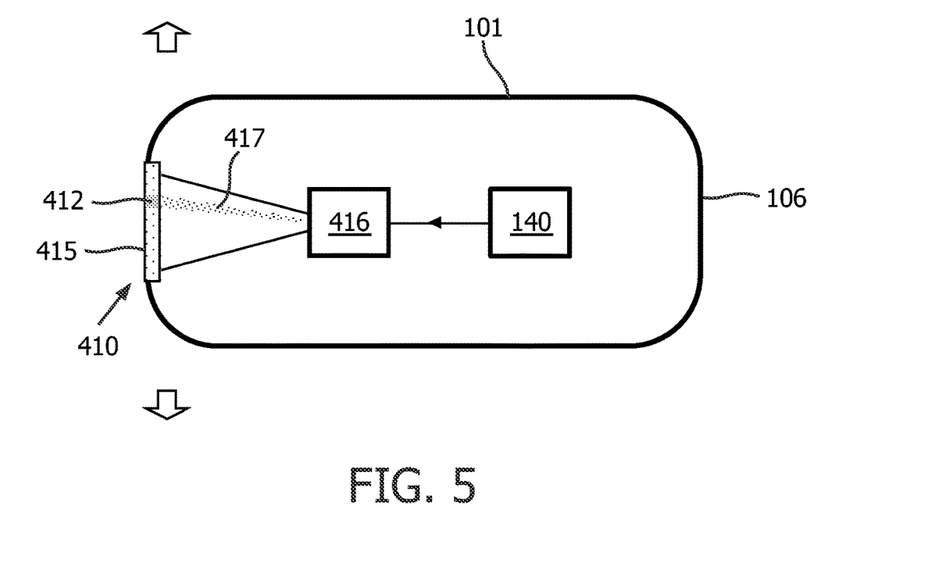
FIG. 5 schematically illustrates a specific embodiment of a handheld skin treatment device according to the invention.

FIG. 5 is a schematic cross sectional top view of an embodiment where the display 410 comprises a partially transparent projection screen 415 and a projection device 416 arranged within the housing 101 and controlled by the control device 140 for projecting a light beam 417 on the projection screen 415. The direction of projection is varied for varying the position where the light beam 417 hits the screen 415.

Figure 6A:
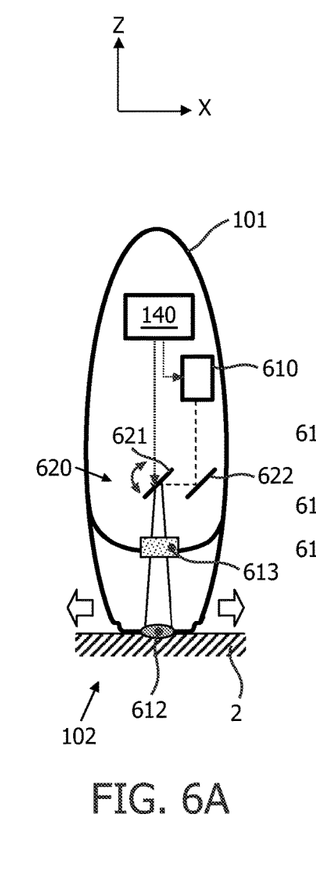
FIGS. 6A-6B represent views, comparable to FIGS. 1B-1C, of another specific embodiment of a handheld skin treatment device according to the invention.
Figure 6B:
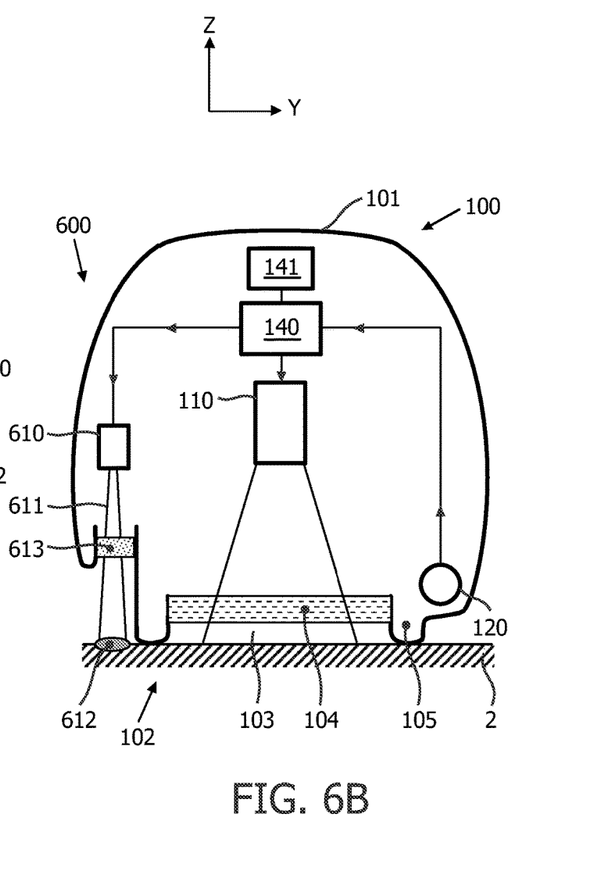

In practice, the user may tend to look more at his skin being treated than at the housing. FIGS. 6A-6B illustrate a preferred embodiment, which has the advantage that the optical spot is located even closer to the user's field of view: in this preferred embodiment, a light spot is projected on the user's skin.

FIG. 6A is a view comparable to FIG. 1B, and FIG. 6B is a view comparable to FIG. 1C, of a skin treatment device 100 comprising a speed deviation indicator system 600 according to the present invention. This skin treatment device 100 obviously also comprises the treatment action performer 110. In this embodiment, the speed deviation indicator system 600 comprises a light beam generator 610 arranged within the housing 101, for generating an indicator light beam 611, and the housing 101 has an indicator window 613 for allowing the indicator light beam 611 to pass such as to exit the housing 101. The light beam generator 610 may direct the indicator light beam 611 directly to the indicator window 613; in FIG. 6A, the speed deviation indicator system 600 comprises an optical system 620 for deflecting the light beam towards the indicator window 613. The indicator light beam 611 passing the indicator window 613 has a substantially vertical component and will hit the skin 2 at a position adjacent the foot 105 of the housing 101, projecting a light spot 612 (optical spot).

The light beam generator 610 may comprise one or more LEDs. The control device 140 may control the light beam generator 610 to vary the colour of the optical spot, in a similar manner as described with respect to the display 410.

The speed deviation indicator system 600 is adapted such that the position of the optical spot 612 relative to the housing 101 can be varied. To this end, it is possible that the orientation of the light beam generator 610 itself can be varied. In the embodiment shown, the light beam generator 610 is fixed in the housing 101, and the optical system 620 comprises at least one movable optical component, in this case a rotatable mirror 621. In the embodiment shown, the optical system 620 also comprises a fixed mirror 622. The position of the rotatable mirror 621 is controlled by the control device 140. It should be clear that rotating the mirror 621 clockwise in the drawing will result in the optical spot 612 being displaced to the left in the drawing, and vice versa.

In a similar manner as described earlier, the control device 140 compares the sensor output signal with the desired speed stored in the memory. If the user is displacing the skin treatment device 100 too slowly, the control device 140 controls the rotatable mirror 621 such that the optical spot 612 is projected in front of the housing 101, at a larger distance as the speed deviation is larger. If the user is displacing the skin treatment device 100 too fast, the control device 140 controls the rotatable mirror 621 such that the optical spot 612 is projected behind the housing 101, at a larger distance as the speed deviation is larger. Here, "in front of" and "behind" are related to the displacement direction. The housing 101 itself functions as reference. The actual speed control is done by the user, who should keep the skin treatment device 100 adjacent the optical spot, which works very intuitively in practice.

Although the present invention is already embodied by a skin treatment device 100 wherein one optical spot 612 is projected on the skin adjacent the housing, in a preferred embodiment of the skin treatment device 100, such optical spots are projected on the skin on opposite sides of the housing. The speed deviation indicator system 600 may comprise two light beam generators 610 for generating two respective indicator light beams 611, and may have two respective optical systems 620 for deflecting the respective indicator light beams 611, all of which are controlled by one common control device 140. It is also possible that the speed deviation indicator system 600 comprises one common light beam generator 610 for generating one light beam that is split up to generate the two light spots.

Summarizing, the present invention provides a skin treatment device which can be displaced very easily and intuitively over the skin at a correct speed.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appending claims.

For instance, other possible designs for displacing an optical spot over a projection surface will readily become apparent to a skilled person after reading the above explanation.

Further, although an embodiment with continuously variable optical spot position is preferred, an embodiment where the optical spot only has a discrete number of possible positions is also possible. This number may even be equal to 3, just indicating "too high", "OK", "too low".

Further, although it is preferred that the control device 140 is adapted to control the treatment action performer 110, this is not essential for implementing the present invention.

Further, the optical spot 412, 612 may have a specially designed shape differing from circular, for instance arrow-shaped, in order to further contribute to the comfortable and intuitive manner in which the user is informed of what he must do: speed up or speed down.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. Even if certain features are recited in different dependent claims, the present invention also relates to an embodiment having these features in common. Any reference signs in the claims should not be construed as limiting the scope.

In the above, the present invention has been explained with reference to block diagrams, which illustrate functional blocks of the device according to the present invention. It is to be understood that one or more of these functional blocks may be implemented in hardware, where the function of such a functional block is performed by individual hardware components, but it is also possible that one or more of these functional blocks are implemented in software, so that the function of such one or more functional blocks is performed by one or more program lines of a computer program or a programmable device such as a microprocessor, microcontroller, digital signal processor, etc.

The invention claimed is:

1. A skin treatment device, comprising:
    a housing the shape and size of which are such that it can suitably be held by a human hand, the housing having a skin-side to be directed to a user's skin and an output window arranged on the skin-side;
    a treatment action performer arranged within the housing for performing a continuous treatment action on the user's skin through the output window as the skin-side of the housing is displaced continuously over the user's skin;
    a speed sensor for sensing a relative speed between the housing and the user's skin in a device displacement direction (X) parallel to the skin;
    an optical speed deviation indicator system for generating at least one optical spot (i) within a user's field of view while the user is looking at a position where the housing touches the user's skin, (ii) representative of a magnitude and direction of a deviation between (ii)(a) a displacement speed or speed range of the housing as the housing is being displaced continuously over the user's skin and (ii)(b) a desired displacement speed or a desired displacement speed range, and (iii) at a speed deviation indicator position with respect to a position reference of the housing that comprises at least one of (iii)(a) a reference mark arranged on a side surface of the housing or (iii)(b) the housing itself, wherein the speed deviation indicator position of the at least one optical spot is a variable position with respect to the position reference of the housing; and
    a control device provided with an associated memory containing information defining the desired displacement speed or the desired displacement speed range, the control device being coupled to receive an output signal from the speed sensor and being coupled to provide a control signal to the optical speed deviation indicator system;
    wherein the control device is adapted to control the optical speed deviation indicator system to vary the speed deviation indicator position of the at least one optical spot based on (i) the output signal received from the speed sensor and (ii) the information in the memory.

2. The skin treatment device according to claim 1, wherein said at least one optical spot is displaceable with respect to said position reference in a direction parallel to said device displacement direction (X);
    wherein the control device is adapted to control the optical speed deviation indicator system wherein the speed deviation indicator position of the at least one optical spot is located in front of the position reference, relative to the displacement direction (X), if the output signal from the speed sensor indicates that a momentary device displacement speed is below the desired displacement speed or displacement speed range; and
    wherein the control device is adapted to control the optical speed deviation indicator system wherein the speed deviation indicator position of the at least one optical spot is located behind the position reference, relative to the displacement direction (X), if the output signal from the speed sensor indicates that the momentary device displacement speed is above the desired displacement speed or displacement speed range.

3. The skin treatment device according to claim 2, wherein the control device is adapted to control the optical speed deviation indicator system wherein a distance between the speed deviation indicator position of the at least one optical spot and said position reference, measured in the direction parallel to said device displacement direction (X), is proportional to a speed difference between the momentary device displacement speed and the desired displacement speed.

4. The skin treatment device according to claim 1, wherein the control device is adapted to change a colour of the at least one optical spot in conjunction with the speed deviation indicator position of the at least one optical spot.

5. The skin treatment device according to claim 1, wherein the at least one optical spot is projected on the user's skin.

6. The skin treatment device according to claim 1, wherein the optical speed deviation indicator system comprises:

an indicator light beam generator arranged within the housing, for generating an indicator light beam; and an indicator window in the housing for allowing the indicator light beam to pass and exit the housing, wherein the indicator window is located proximate to the output window such that, in use, the indicator light beam will meet the user's skin to produce said at least one optical spot;

wherein a direction of the indicator light beam is varied such as to vary the speed deviation indicator position of the at least one optical spot.

7. The skin treatment device according to claim 6, wherein the indicator light beam generator comprises one or more LEDs.

8. The skin treatment device according to claim 6, wherein the optical speed deviation indicator system comprises at least one movable optical component controlled by the control device for changing the direction of the indicator light beam.

9. The skin treatment device according to claim 1, wherein the at least one optical spot is produced on the housing.

10. The skin treatment device according to claim 9, wherein the optical speed deviation indicator system further comprises:

a display located on the housing; and wherein the position reference comprises the reference mark arranged on the housing.

11. The skin treatment device according to claim 10, wherein the display comprises a row of LEDs which can be switched on or off individually, wherein the control device decides which LED in the row of LEDs to switch on, based on the output signal from the speed sensor.

12. The skin treatment device according to claim 10, wherein the display comprises a partially transparent projection screen, and a projection device arranged within the housing and controlled by the control device for projecting a light beam on the projection screen.

13. The skin treatment device according to claim 10, wherein the display comprises two displays, one display each in opposite side faces of the housing.

14. The skin treatment device according to claim 1, wherein the control device is further adapted to control the treatment action performer based on the output signal received from the speed sensor and the information in the memory, wherein an intensity of the treatment action performed by the treatment action performer is reduced if the output signal from the speed sensor indicates that a momentary device displacement speed is below the desired displacement speed or displacement speed range.

15. An optical epilation device comprising the skin treatment device according to claim 1, wherein the treatment action performer comprises a device for illuminating the user's skin with continuous light or with a scanning light beam or with high-frequency light flashes.

16. The skin treatment device according to claim 1, wherein the at least one optical spot further includes at least one arrow-shaped spot configured to inform the user to speed up or speed down the displacement speed of the housing being displaced continuously over the user's skin.

17. The skin treatment device according to claim 5, wherein the at least one optical spot further comprises two optical spots projected on opposite sides of the housing.

18. The skin treatment device according to claim 8, wherein the at least one movable optical component comprises a rotatable mirror.

19. The skin treatment device according to claim 9, wherein the at least one optical spot further comprises two optical spots projected on opposite sides of the housing.

20. The skin treatment device according to claim 10, wherein the display is further located on a side surface of the housing and the reference mark is arranged on the side surface.

* * * * *